United States Patent [19]

Matsumoto

[11] Patent Number: 4,500,533

[45] Date of Patent: Feb. 19, 1985

[54] 2,4,5-TRIARYL PYRIMIDINES AND A METHOD OF TREATING PAIN, FEVER, THROMBOSIS, INFLAMMATION AND ARTHRITIS

[75] Inventor: Ken Matsumoto, Indianapolis, Ind.

[73] Assignee: Eli Lilly and Company, Indianapolis, Ind.

[21] Appl. No.: 506,932

[22] Filed: Jun. 22, 1983

[51] Int. Cl.³ .................. A61K 31/505; C07D 239/02
[52] U.S. Cl. ..................................... 514/256; 544/335
[58] Field of Search ......................... 544/335; 424/251

[56] References Cited

U.S. PATENT DOCUMENTS

| | | | |
|---|---|---|---|
| 3,558,626 | 1/1971 | Griot | 544/335 |
| 3,758,462 | 9/1973 | Siegrist | 544/335 |
| 4,153,703 | 5/1979 | Harrison | 424/270 |
| 4,168,315 | 9/1979 | Rynbrandt et al. | 424/270 |
| 4,197,306 | 4/1980 | Harrison | 424/270 |
| 4,322,428 | 3/1982 | Matsumoto et al. | 424/270 |
| 4,330,552 | 5/1982 | Cherkofsky | 424/273 R |

FOREIGN PATENT DOCUMENTS 5219 11/1979 European Pat. Off. .

OTHER PUBLICATIONS

*J. Heterocyclic Chem.*, 19, 1165 (1982).
*Journal of Medicinal Chemistry*, 24, 1507 (1981).
Derwent E/40 84068, abstracting European Patent Application 61,425.

*Primary Examiner*—Donald G. Daus
*Assistant Examiner*—Cecilia Shen
*Attorney, Agent, or Firm*—Charles W. Ashbrook; Arthur R. Whale

[57] ABSTRACT

This invention provides for certain novel 2,4,5-triaryl pyrimidine derivatives, their pharmaceutical formulations, and a method of treating pain, fever, thrombosis, inflammation, and arthritis.

14 Claims, No Drawings

2,4,5-TRIARYL PYRIMIDINES AND A METHOD OF TREATING PAIN, FEVER, THROMBOSIS, INFLAMMATION AND ARTHRITIS

BACKGROUND OF THE INVENTION

It is an object of this invention to provide novel 2-phenyl-4,5-bis(4-methoxyphenyl)pyrimidine derivatives. These compounds are active as prostaglandin synthetase inhibitors, analgesic agents, anti-inflammatory agents, anti-arthritic agents, anti-pyretic agents, and antithrombotic agents.

Certain 2-arylthio-4,5-bis(4-methoxyphenyl)-pyrimidines are taught in the art to be less active as anti-inflammatory agents than the corresponding imidazole compounds. See *J. Het. Chem.*, 19, 1162 (1982).

SUMMARY OF THE INVENTION

This invention provides for compounds of the Formula I

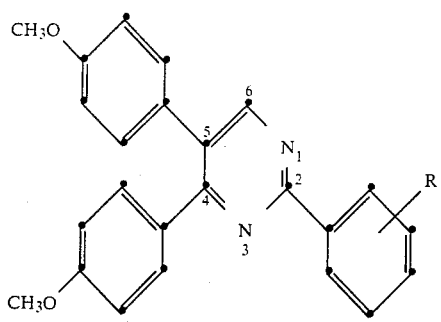

and pharmaceutically acceptable salts thereof, wherein R is hydrogen, trifluoromethyl, fluoro, chloro, bromo, or iodo.

Further provided by this invention are pharmaceutical formulations for these compounds and a method for treating pain, fever, thrombosis, inflammation, and arthritis in mammals using compounds of Formula I or their pharmaceutical formulations.

DETAILED DESCRIPTION AND PREFERRED EMBODIMENT

The present invention relates to new organic compounds that are useful in the treatment of pain, fever, thrombosis, inflammation, and arthritis in mammals. The compounds of Formula I are chemically known as 2-phenyl-4,5-bis(4-methoxyphenyl)pyrimidines. A preferred group of compounds are the compounds of Formula I wherein R is bromo, chloro, or fluoro. Especially preferred compounds are those wherein the halo substituents are substituted at the 4-position of the phenyl ring.

The compounds of this invention can be prepared by the following reaction scheme:

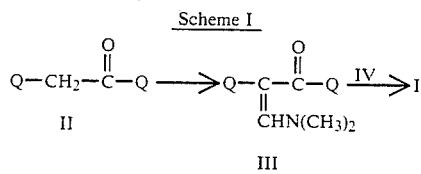

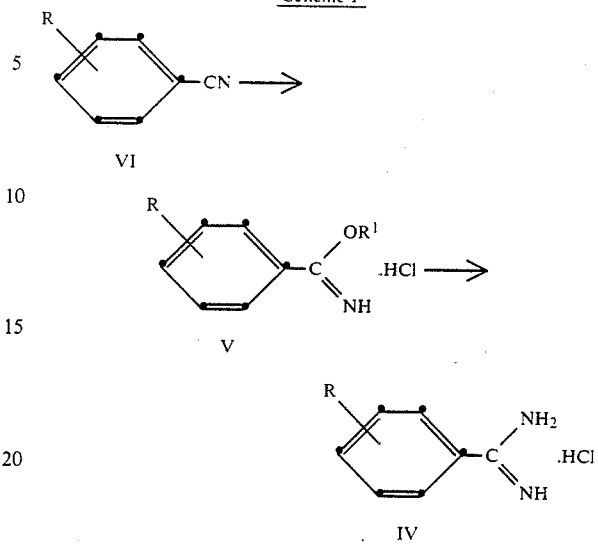

where Q is 4-methoxyphenyl, R is the same as previously defined, and $R^1$ is $C_1$-$C_4$ alkyl.

According to Scheme I, commercially available desoxyanisoin II is converted to enaminone III. This enaminone is known in the art (*J. Het. Chem.*, 19, 1165 (1982)) where it was prepared by heating desoxyanisoin with bis(dimethylamino)-t-butoxymethane in dimethylformamide. Alternatively, the enaminone can be prepared by heating desoxyanisoin to reflux with a dimethylformamide dialkyl acetal preferably in the absence of any other solvent. The enaminone is then allowed to react with the desired benzamidine IV to give the corresponding product I. The reaction of the enaminone and the benzamidine is carried out in a non-reactive solvent, such as benzene or toluene, at elevated temperatures, preferably the reflux temperature of the reaction mixture. In addition, the reaction requires the addition of a base such as sodium hydride or preferably potassium t-butoxide. One molar equivalent of base is employed for the reaction; an additional molar equivalent is used if the amidine is used in the salt form.

The amidine intermediates IV are prepared from the corresponding imino esters V which are in turn prepared from the appropriate benzonitrile derivatives VI. This nitrile/imino ester/amidine transformation is the standard Pinner reaction amidine synthesis where a nitrile is converted to the imino ester in the presence of an alcohol (R'OH) and dry hydrogen chloride gas. Treatment of the imino ester with ammonia affords the corresponding amidine which is usually isolated as an acid addition salt.

The trifluoromethyl derivatives of this invention may also be prepared by heating the corresponding aryl iodide with bis(trifluoromethyl)mercury, copper, and N-methyl-2-pyrrolidinone.

The starting materials and reagents required for the preparation of the compounds of Formula I are either commercially available, are known in the art, or can be prepared by methods known in the art.

The pharmaceutically acceptable acid addition salts of this invention include salts derived from inorganic acids such as hydrochloric acid, nitric acid, phosphoric acid, sulfuric acid, hydrobromic acid, hydriodic acid, and the like, as well as salts derived from nontoxic strong organic acids such as aliphatic and aromatic sulfonic acids. Such pharmaceutically acceptable salts thus include sulfate, nitrate, chloride, bromide, iodide, benzenesulfonate, toluenesulfonate, chlorobenzenesulfonate, xylenesulfonate, methanesulfonate, propanesulfonate, naphthalene-1-sulfonate, naphthalene-2-sulfonate, and the like salts.

The compounds of this invention may be administered by various routes including the oral, rectal, transdermal, subcutaneous, intravenous, intramuscular, or intranasal routes, being usually employed in the form of a pharmaceutical composition, although it is a special feature of these compounds that they are effective following oral administration. Such compositions are prepared in a manner well known in the pharmaceutical art and comprise at least one active compound. Accordingly, the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The oral absorption of the novel compounds of this invention in mammals is greatly enhanced by administering the compounds of Formula I in a lipid-containing vehicle. Lipid vehicles include oils, oil emulsions, sterol esters, waxes, vitamin A esters, vegetable oils such as corn oil, coconut oil, and safflower oil, animal fats such as lard and spermaceti, phospholipids, and synthetic triglycerides such as Medium Chain Triglycerides (MCT-$C_8$-$C_{10}$ chain) and Long Chain Triglycerides (LCT-$C_{16}$-$C_{18}$ chain).

Excipients can also be added and include glycols, such as polyethylene glycol and polypropylene glycol, cellulose, starch, and the like.

Although oil alone can be used to administer the compound, if the mammal receiving the compound-oil mixture can rapidly digest and absorb the oil, an oil emulsion is the preferred method of administration. The preferred oil emulsion is a corn oil-acacia emulsion, formed by dissolving the compound in corn oil and then emulsifying the mixture with a ten percent acacia solution.

Other emulsifiers or emulsifying agents can include natural emulsifiers, such as acacia, phospholipids such as lecithin, gelatin, and cholesterol, and synthetic emulsifiers such as glyceryl esters, like glyceryl monostearate, sorbitan fatty acid esters, like sorbitan monopalmitate (Span 40), polyoxyethylene sorbitan fatty acid esters, like polyoxyethylene sorbitan monopalmitate (Tween 40) and polyoxyethylene sorbitan monooleate (Tween 80), and polyoxyethylene glycol esters, like polyoxyethylene glycol monostearate.

Other methods of administration include fluid or solid unit dosage forms, such as capsules, slurries, suspensions, and the like. For example, one form is a hard gelatin capsule containing the compound dissolved in fat. First, the compound is dissolved in the fat, while the fat is in a liquid state, and the mixture is then solidified, resulting in a homogenous amorphous solution. The mixture is then pulverized and placed in a hard gelatin capsule. An emulsifier can also be added to the mixture, if desired.

Alternatively, fluid unit dosage forms, such as soft gelatin capsules, can be used to administer the compounds. These capsules are prepared by machine encapsulation of a slurry of the compound and an acceptable lipid vehicle. A slurry alone without encapsulation can also be administered.

Still another fluid unit dosage form is a suspension, which is prepared with a syrup vehicle aided by a suspending agent, such as acacia, tragacanth, methylcellulose, and the like.

A further method of administration is to orally administer the compound to a mammal previously fed a fatty meal, thereby using the fats consumed in the meal as the lipid-containing vehicles. Before the compound is administered to the mammal, the compound is micronized and coated with a surfactant, such as acacia.

Therefore, one preferred aspect of this invention is a pharmaceutical formulation comprising an effective amount of a compound of Formula I in combination with a pharmaceutically acceptable lipid-containing vehicle. A surfactant or emulsifier can also be added to the formulation.

Another preferred aspect of this invention is a pharmaceutical formulation comprising an effective amount of a compound of Formula I in combination with a pharmaceutically acceptable surfactant-containing vehicle. This formulation is administered with or after the mammal has a fatty meal.

Preferably the compositions are formulated in a unit dosage form, each dosage containing from about 5 to 500 mg., more usually about 25 to 300 mg., of the active ingredient. The term "unit dosage form" refers to physically discrete units suitable as unitary dosages for mammals, including human subjects, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. In the treatment of adult humans, the range of about 1 to 50 mg./kg., in single or divided doses, is preferred. However it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following preparations and examples further illustrate the preparation of the starting materials, intermediates, and compounds of this invention. The examples are illustrative only and are not intended to limit the scope of the invention in any way.

EXAMPLE 1

2-(4-Chlorophenyl)-4,5-bis(4-methoxyphenyl)pyrimidine

A. Preparation of (4-methoxyphenyl)[1-(4-methoxyphenyl)-2-dimethylaminovinyl]ketone.

A suspension of 5.23 g. of desoxyanisoin in 25 ml. of N,N-dimethylformamide dimethyl acetal was heated to reflux for 22 hours. The solids went into solution at reflux but on cooling a suspension reappeared. The solvent was removed in vacuo to provide the desired tital intermediate which was used without further purification for the subsequent reaction. A portion was crystallized from Skelly B to provide the purified intermediate.

Analysis: $C_{19}H_{21}NO_3$; Calc.: C, 73.29; H, 6.80; N, 4.50; Found: C, 73.04; H, 6.53; N, 4.34.

B. Preparation of ethyl 4-chlorobenzimidate hydrochloride.

A suspension of 47.0 g. of 4-chlorobenzonitrile in 600 ml. of ethanol was cooled by means of an external ice-alcohol bath. Dry hydrogen chloride gas was bubbled into the reaction mixture for four hours while the temperature was held below 10° C. The reaction turned from a suspension to a yellow solution. After gas addition was stopped, the solution was placed in a refrigerator overnight. The solution was filtered and evaporated in vacuo to afford 63.53 g. of the desired title intermediate, m.p. about 170°–173° C.

C. Preparation of 4-chlorobenzamidine hydrochloride.

A solution of 25.0 g. of ethyl 4-chlorobenzimidate hydrochloride in 100 ml. of methanol was cooled to −78° C. by means of an external acetone/dry ice bath. To the solution were added approximately 75 ml. of liquified ammonia. The reaction was allowed to come to room temperature and was stirred overnight. The solution was then evaporated to dryness and the residue was dissolved in 150 ml. of ethanol. The solution was poured into 800 ml. of ethyl acetate. The resulting precipitate was recovered by filtration to afford 18.86 g. of the desired title intermediate, m.p. about 240°–245° C.

Analysis: $C_7H_8Cl_2N_2$; Calc.: C, 44.01; H, 4.22; N, 14.66; Cl, 37.11; Found: C, 43.78; H, 4.47; N, 14.55; Cl, 36.86.

D. Preparation of 2-(4-chlorophenyl)-4,5-bis(4-methoxyphenyl)pyrimidine.

A suspension of 9.34 g. of (4-methoxyphenyl)-[1-(4-methoxyphenyl)-2-dimethylaminovinyl]ketone, 5.73 g. of 4-chlorobenzamidine hydrochloride, and 6.73 g. of potassium t-butoxide in 200 ml. of toluene was allowed to reflux for 2.5 hours and then stirred overnight at room temperature. The suspension was extracted twice each with 200 ml. of water. The combined water extracts were back-extracted with 100 ml. of toluene. The combined toluene solutions were washed with 100 ml. of a saturated sodium chloride solution. The organic solution was then dried over sodium sulfate and evaporated in vacuo. The residue was purified by chromatography over silica gel. The appropriate fractions were evaporated to dryness and crystallized from Skelly B to provide 3.97 g. of the desired title product, m.p. about 151°–153° C.

Analysis: $C_{24}H_{19}ClN_2O_2$; Calc.: C, 71.55; H, 4.75; N, 6.95; Cl, 8.80; Found: C, 71.80; H, 4.62; N, 6.97; Cl, 9.05.

EXAMPLE 2

2-(4-Fluorophenyl)-4,5-bis(4-methoxyphenyl)pyrimidine

Starting with 4-fluorobenzonitrile, the title product was prepared following the procedure of Example 1, m.p. about 129°–130° C.

Analysis: $C_{24}H_{19}FN_2O_2$; Calc.: C, 74.60; H, 4.96; N, 7.25; Found: C, 74.87; H, 5.15; N, 7.28.

The following formulation examples may employ as active compounds any of the pharmaceutical compounds of this invention.

EXAMPLE 3

Hard gelatin capsules are prepared using the following ingredients:

|  | Quantity (mg./capsule) |
| --- | --- |
| Active compound | 250 |
| Starch dried | 200 |
| Magnesium stearate | 10 |

The above ingredients are mixed and filled into hard gelatin capsules in 460 mg. quantities.

EXAMPLE 4

A tablet formula is prepared using the ingredients below:

|  | Quantity (mg./tablet) |
| --- | --- |
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 5

An aerosol solution is prepared containing the following components:

|  | Weight % |
| --- | --- |
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remainder of the propellant. The valve units are then fitted to the container.

EXAMPLE 6

Tablets each containing 60 mg. of active ingredient are made up as follows:

| | |
|---|---|
| Active ingredient | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 7

Capsules each containing 80 mg of medicament are made as follows:

| | |
|---|---|
| Active ingredient | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 8

Suppositories each containing 225 mg. of active ingredient are made as follows:

| | |
|---|---|
| Active ingredient | 225 mg. |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 9

Suspensions each containing 50 mg. of medicament per 5 ml. dose are made as follows:

| | |
|---|---|
| Active ingredient | 50 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention are useful as prostaglandin synthetase inhibitors, analgesic agents, anti-inflammatory agents, anti-arthritic agents, antipyretic agents, and antithrombotic agents. The compounds are especially useful as analgesic and anti-inflammatory agents. In addition, the compounds have been demonstrated to have a low potential for phototoxic side effects.

The analgesic activity of a number of compounds provided by this invention has been determined in the standard mouse writhing assay. Writhing, which is characterized by contraction of the abdominal musculature, extension of the hindlegs, and rotation of the trunk, was induced in Cox standard strain albino male mice. The mice, weighing 18–24 grams, were fasted overnight and given the test compound by gavage in a corn oil-acacia emulsion (5%) three hours before writhing was induced by the intraperitoneal administration of acetic acid (0.60 percent). Each treatment group consisted of five mice. The total number of writhes for the treatment group was determined during a 10 minute observation starting five minutes after acetic acid administration. Control groups had a total of 40–60 writhes per observation period. Table I which follows presents typical test results obtained with certain of the compounds of this invention. The results in the mouse writhing assay are presented as the effective oral (p.o.) dose in mg./kg. of the tested compound required to inhibit induced writhing in the test animals by fifty percent ($ED_{50}$).

TABLE I

| Compound of Example No. | Mouse Writhing $ED_{50}$ (mg./kg. p.o.) |
|---|---|
| 1 | 0.99 |
| 2 | 1.48 |

Established adjuvant-induced arthritis test in rats

Certain compounds of this invention were tested for their ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary injected hind paw, and (2) the secondary uninjected hind paw, which generally begins developing about eleven days from the induction of inflammation in the injected paw.

One group of five rats received no treatment (normal control). Adjuvant arthritis was induced in male Lewis-Wistar rats (200–210 grams) on test day one by a single subplantar injection into the right hind paw of 0.1 ml. of a 0.5% suspension of heat-killed, lyophilized *Mycobacterium tuberculosis* (Calbiochem-Perrigen-C) in mineral oil (a modification of a method reported by Winter et al., *Arth. Rheum.*, 9, 394–397 (1966)). Only animals in which the non-injected paw measured at least a volume of 0.5 ml. greater than normal control animals on day 14 were selected for the rest of the experiment. One group of ten rats ("TB control") received no further treatment. Each compound to be tested was administered as a corn oil-acacia emulsion by gavage to rats (groups of five each) in daily oral doses, beginning on day 15 and continuing through the 29th day after the adjuvant injection (15 doses). Paw volumes were measured by mercury displacement using a Statham pressure transducer and digital voltmeter. Volumes of both the injected and the uninjected hind paws were measured on days 14, 16, 18, 21, 23, 25, 28, and 30. The paw volume measurements of the uninjected paw beginning with day 14 through day 30 were computer plotted for the TB controls, the normal controls, and the drug-treated animals, and the areas under the curves [(TB controls minus normal controls) and (drug-treated animals minus normal controls)] were determined. The results are summarized in Table II.

TABLE II

| Inhibition of Uninjected Paw Volume Inflammation Days 14 through 30 | | |
|---|---|---|
| Compound of Example No. | Dose (mg./kg. p.o. × 15) | % Inhibition* |
| 1 | 25 | 74 |
| 2 | 10 | 70 |

*% inhibition is the difference of the areas under the curves (AUC) of the mean uninjected paw volumes plotted for days 14, 16, 18, 21, 23, 25, 28, and 30 according to the following formula:
% inhibition =

$$\left[ 1 - \frac{(\text{Drug treated AUC}) - (\text{normal control AUC})}{(\text{TB control AUC}) - (\text{normal control AUC})} \right] \times 100$$

I claim:
1. A compound of the formula

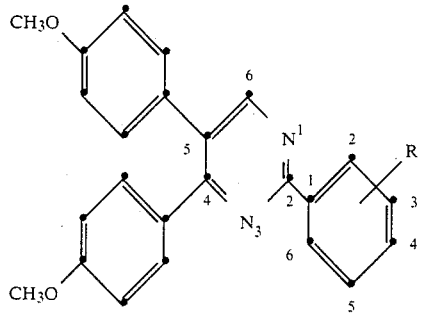

and pharmaceutically acceptable salts thereof, wherein R is hydrogen, trifluoromethyl, fluoro, chloro, bromo, or iodo.

2. A compound of claim 1 wherein R is at the 4-position of the phenyl ring.

3. The compound of claim 2 which is 2-(4-fluorophenyl)-4,5-bis(4-methoxyphenyl)pyrimidine or a pharmaceutically acceptable salt thereof.

4. The compound of claim 2 which is 2-(4-chlorophenyl)-4,5-bis(4-methoxyphenyl)pyrimidine or a pharmaceutically acceptable salt thereof.

5. A method of treating pain, fever, thrombosis, inflammation, or arthritis which comprises administering to a mammal in need of such treatment an effective amount of a compound of claim 1.

6. The method of claim 5 wherein the compound is 2-(4-fluorophenyl)-4,5-bis(4-methoxyphenyl)-pyrimidine or a pharmaceutically acceptable salt thereof.

7. The method of claim 5 wherein the compound is 2-(4-chlorophenyl)-4,5-bis(4-methoxyphenyl)-pyrimidine or a pharmaceutically acceptable salt thereof.

8. A pharmaceutical formulation useful in the treatment of pain, fever, thrombosis, flammation, or arthritis comprising an effective amount of a compound of claim 1 in association with a pharmaceutically acceptable carrier.

9. A formulation of claim 8 which contains a pharmaceutically acceptable lipid-containing vehicle.

10. A formulation of claim 9 which also contains a pharmaceutically acceptable surfactant.

11. A formulation of claim 10 wherein the lipid containing vehicle is an oil emulsion.

12. A formulation of claim 11 wherein the oil emulsion comprises corn oil and acacia.

13. The formulation of claim 12 wherein the compound is 2-(4-fluorophenyl)-4,5-bis(4-methoxyphenyl)-pyrimidine or a pharmaceutically acceptable salt thereof.

14. The formulation of claim 12 wherein the compound is 2-(4-chlorophenyl)-4,5-bis(4-methoxyphenyl)-pyrimidine or a pharmaceutically acceptable salt thereof.

* * * * *